US008604087B2

(12) United States Patent
Kim et al.

(10) Patent No.: US 8,604,087 B2
(45) Date of Patent: Dec. 10, 2013

(54) COMPOSITION FOR TREATING OR PREVENTING AMYLOID-RELATED DISEASES COMPRISING 4-O-METHYLHONOKIOL

(75) Inventors: Ki Ho Kim, Cheonan-si (KR); Ki Soo Kim, Cheongju-si (KR); Young Heui Kim, Cheonan-si (KR); Jin Guk Kim, Cheonan-si (KR); Kyoung Tae Kim, Asan-si (KR); Chang Sung Han, Cheonan-si (KR); Sang iL Lee, Cheonan-si (KR)

(73) Assignee: Bioland Ltd. (KR)

( * ) Notice: Subject to any disclaimer, the term of this patent is extended or adjusted under 35 U.S.C. 154(b) by 192 days.

(21) Appl. No.: 13/120,818

(22) PCT Filed: Sep. 25, 2009

(86) PCT No.: PCT/KR2009/005485
§ 371 (c)(1),
(2), (4) Date: Mar. 24, 2011

(87) PCT Pub. No.: WO2010/036052
PCT Pub. Date: Apr. 1, 2010

(65) Prior Publication Data
US 2011/0207830 A1 Aug. 25, 2011

(30) Foreign Application Priority Data

Sep. 25, 2008 (KR) .................. 10-2008-0094273
Sep. 25, 2008 (KR) .................. 10-2008-0094320

(51) Int. Cl.
A01N 31/04 (2006.01)
A01N 31/08 (2006.01)

(52) U.S. Cl.
USPC .......................................... 514/721; 514/734

(58) Field of Classification Search
USPC ................................................. 514/721, 734
See application file for complete search history.

(56) References Cited

U.S. PATENT DOCUMENTS 5,053,548 A * 10/1991 Tanaka et al. .................. 568/47
2005/0027004 A1* 2/2005 Kyle et al. ..................... 514/560

FOREIGN PATENT DOCUMENTS

KR 10-2009-0094916 9/2009

OTHER PUBLICATIONS

Stix, Gary "Alzheimer's: Forestalling the Darkness", Scientific American, Jun. 2010, pp. 51-57.*

Tada et al. "Intestinal pseudo-obstruction in patients with amyliodosis: clinicopathologic differences between chemical types of amyloid protein" Gut, 1993, vol. 34, pp. 1412-1417.*
Sam Gandy, "The role of cerebal amyloid B Accumulation in common forms of Alzheimer disease," The Journal of Clinical Investigation, vol. 115, No. 5, May 2005, pp. 1121-1129.
Laura Gasparini, "Activity of flurbiprofen and chemically related anti-inflammatory drugs in models of Alzheimer's disease," Brain Research Reviews, vol. 48, 2005, pp. 400-408.
Crystal Pallister et al., "Lymphocyte Content of Amyloid Precursor Protein is Increased in Down's Syndrome and Aging," Neurobiology of Aging, vol. 18. No. 1, 1997, pp. 97-103.
Yasuhiro Arai et al., "Developmental and aging changes in the expression of amyloid precursor protein in Down syndrome brains," Brain & Development, vol. 19, 1997, pp. 290-294.
James K. Nitao et al., "Bioactive Neolignans from the leaves of *Magnolia virginiana*," Phytochemistry, vol. 30, No. 7, 1991, pp. 2193-2195.
David H. Small, "Mechanisms of Synaptic Homeostasis in Alzheimer's Disease," Current Alzheimer Research, vol. 1, No. 1, 2004, pp. 27-32.
Yoshiyasu Fukuyama et al., "Neurotrophic Sesquiterpene-Neolignans from *Magnolia obovata*: Structure and Neurotrophic Activity," Tetrahedron, vol. 48, No. 3, 1992, pp. 377-392.
Shoji Yahara et al., "Isolation and Characterization of Phenolic Compounds from *Magnoliae* Cortex Produced in China," Chem. Pharm. Bull, vol. 39, No. 8, 1991, pp. 2024-2036.
Concetta M. Forchetti, "Treating Patients With Moderate to Severe Alzheimer's Disease: Implications of Recent Pharmacologic Studies," Prim Care Companion J Clin Psychiatry vol. 7, No. 4, 2005, pp. 155-161.
F.S. El-Feraly et al., "Isolation and Characterization of Magnolol, Honokiol and Honokiol Monomethyl Ether from *Magnolia grandiflora* L. Seeds," Lloydia, 1978, 653.
Xiongwei Zhu et al., "Oxidative stress signalling in Alzheimer's disease," Brain Research, vol. 1000, 2004, pp. 32-39.

* cited by examiner

*Primary Examiner* — Kendra D Carter
(74) *Attorney, Agent, or Firm* — Cantor Colburn LLP

(57) ABSTRACT

Disclosed is a composition for treating or preventing amyloid-related diseases including 4-O-methylhonokiol as an active ingredient. More specifically, a pharmaceutical composition including 4-O-methylhonokiol, which is effective for treating or preventing amyloid-related diseases such as Alzheimer's disease, cognitive disorder, defective memory, amyloidosis, etc. is disclosed. The inventors of the present disclosure have found out for the first time that 4-O-methylhonokiol inhibits the production of β-amyloid. It has been confirmed to be useful in treating or preventing amyloid-related diseases. Through animal tests including water maze test and passive avoidance test on mice, 4-O-methylhonokiol has been confirmed to be effective for amyloid-related diseases such as Alzheimer's disease, defective memory, cognitive disorder, and the like. It was further confirmed through acetylcholinesterase activity inhibition test using mouse brain cortex and hippocampus tissue that they are particularly effective in treating or preventing Alzheimer's disease among the amyloid-related diseases.

8 Claims, No Drawings

COMPOSITION FOR TREATING OR PREVENTING AMYLOID-RELATED DISEASES COMPRISING 4-O-METHYLHONOKIOL

TECHNICAL FIELD

The present invention relates to a composition for treating or preventing amyloid-related diseases including 4-O-methylhonokiol as an active ingredient. More particularly, it relates to a pharmaceutical or functional food composition including 4-O-methylhonokiol or a pharmaceutically acceptable salt thereof as an active ingredient, which is useful for treating or preventing amyloid-related diseases, including Alzheimer's disease, cognitive disorder, defective memory, amyloidosis, etc.

BACKGROUND ART

Recently, with the rapid increase of aged population, Alzheimer's disease has become an important social issue. Alzheimer's disease is a serious social and economical concern which devastates the patient's life and ruins those of his/her families. According to the Alzheimer's Association, 10.3% of the people aged 65 years or above are suffering from dementia, and 95 billion dollars are expended every year in treating dementia. And, according to a report by the Korea Health Industry Development Institute, the prevalence of the illness is about 8.3% of the people aged 65 years or above, with more than 340,000, in Korea, as of 2000 (reported on May 10, 2005 in Seoul Shinmun).

Dementia is defined as the decline in memory and cognitive function thereby causing troubles in daily activities. It may be largely classified into vascular dementia and senile dementia. Vascular dementia is associated with cerebral hemorrhage, stroke, etc. mainly caused thrombosis. It is known that memory loss or other symptoms occur as the brain cells around the hemorrhage site are damaged. Senile dementia, a.k.a. Alzheimer's disease, prevails over vascular dementia in frequency, and is known to be caused by the accumulation of β-amyloid in the brain and the continued damage of nerve cells resulting from its toxicity [Gandy et al., *J. Clin. Invest.*, 2005]. It is reported that oxygen radicals play an important function in the process [Zhu et al., *Brain Research*, 2004]. It is also reported that inflammatory response is related with the onset of Alzheimer's disease, which is evidenced by the fact that the occurrence of Alzheimer's disease decreases when non-steroidal anti-inflammatory drugs are administered [Gasparini et al., *Brain Research Reviews*, 2005].

Down's syndrome is a genetic disorder caused by the presence of an extra 21st chromosome. As it is reported that a larger amount of amyloid protein is accumulated in the brains of Down's syndrome patients than normal people, amyloid is known to be related with Down's syndrome [Crystal et al., *Neurobiology of Aging*, 1997, Yasuhiro et al., *Brain & Development*, 1997].

Defective memory, which is one of the symptoms of Alzheimer's disease, is reported to be closely related with the cholinergic nervous system. Exposure to organophosphorus compounds at low concentration induces abnormal activation of acetylcholinesterase, leading to decreased acetylcholine and inefficient transmission thereof. It is also reported that accumulation of β-amyloid causes toxicity in the brain cells and lower memory function [Small et al., *Curr. Alzheimer Res.*, 2004].

Mild cognitive impairment is a term coined by neuroscientists to refer to the individuals who have cognitive impairments beyond that expected for their age and education, but that do not interfere significantly with their daily activities. It is considered to be the boundary or transitional stage between normal aging and dementia. Scientists have classified the patients who show poor memory for their age but do not show the symptoms of Alzheimer's disease, and diagnosed them as mild cognitive impairment. Those who are diagnosed with mild cognitive impairment need to get help from experts for more accurate diagnosis and treatment, because these individuals tend to progress to Alzheimer's disease. Recently, a research is under way to see if vitamin E and acetylcholinesterase inhibitor are effective for the patients with mild cognitive impairment. This research monitors if the administration of vitamin E or acetylcholinesterase inhibitor can reduce the percentage of the patients with mild cognitive impairment to progress to Alzheimer's disease.

Amyloidosis is also called amyloid degeneration. The name amyloid comes from the early mistaken identification of the substance as starch (ainylum in Latin). Amyloid is a semitransparent wax. When stained with a purple pigment, it exhibits a red color. The substance is frequently found in blood vessel walls or nearby fibers, between spleen or liver cells, or between interstitial tissues of heart muscles or glossal muscles. When the amyloid proteins are in small quantity, it is called amyloid degeneration. But, when they are abnormally deposited in organs and/or tissues, it is called amyloidosis.

At present, cholinesterase inhibitors, e.g., Tacrine, Aricept and Exelon, which reduce the breakdown of choline at synapses and thereby increase the quantity of choline in the brain, are used to treat or ameliorate Alzheimer's disease. However, the effect is only slight and temporary, and many side effects including liver toxicity are involved [Forchetti et al., *Prim. Care Companion J. Clin. Psychiatry*, 2005].

A large number of research institutes worldwide have tried to find a cure for Alzheimer's disease and other amyloid-related diseases. There have been efforts to find substances that inhibit the generation of β-amyloid or those that inhibit the apoptosis of nerve cells.

4-O-methylhonokiol was first isolated in 1978 [El-Feraly, F. S. et al., Lloydia, 41, p. 493, 1978]. Like magnolol, 4-O-methylhonokiol is known to antibacterial effect and insecticidal effect against mosquito larva and brine shrimp [Nitao J. K. et al., *Phytochemistry*, 30, p. 2193, 1991]. But, there is no research on the treatment or prevention of Alzheimer's disease or other amyloid-related diseases with 4-O-methylhonokiol.

The inventors of the present disclosure have found out for the first time that 4-O-methylhonokiol inhibits the production of β-amyloid. It has been confirmed to be useful in treating or preventing amyloid-related diseases. Through animal tests including water maze test and passive avoidance test on mice, 4-O-methylhonokiol has been confirmed to be effective for amyloid-related diseases such as Alzheimer's disease, defective memory, cognitive disorder, and the like. It was further confirmed through acetylcholinesterase activity inhibition test using mouse brain cortex and hippocampus tissue that they are particularly effective in treating or preventing Alzheimer's disease among the amyloid-related diseases.

DISCLOSURE

This disclosure is directed to providing a composition for treating and preventing amyloid-related diseases including 4-O-methylhonokiol as an active ingredient, which is effective in treating or preventing amyloid-related diseases such as Alzheimer's disease, cognitive disorder, defective memory, amyloidosis, etc. and is safe with few side effects to the human body.

BEST MODE

In an aspect, the present disclosure provides a composition for treating or preventing amyloid-related diseases comprising 4-O-methylhonokiol or a pharmaceutically acceptable salt thereof as active ingredient.

As used herein, the amyloid-related diseases include all the diseases resulting from accumulation, degeneration or toxicity of amyloid. Specifically, the amyloid-related disease may be one selected from a group consisting of Alzheimer's disease, cognitive disorder, defective memory and amyloidosis. More specifically, it is Alzheimer's disease.

The inventors of the present disclosure have found out for the first time that 4-O-methylhonokiol inhibits the production of β-amyloid. It has been confirmed to be useful in treating or preventing amyloid-related diseases. Through animal tests including water maze test and passive avoidance test on mice, 4-O-methylhonokiol has been confirmed to be effective for amyloid-related diseases such as Alzheimer's disease, defective memory, cognitive disorder, and the like. It was further confirmed through acetylcholinesterase activity inhibition test using mouse brain cortex and hippocampus tissue that they are particularly effective in treating or preventing Alzheimer's disease among the amyloid-related diseases. As used herein, treatment means amelioration or improvement of symptoms.

Specifically, the 4-O-methylhonokiol may be represented by the following formula:

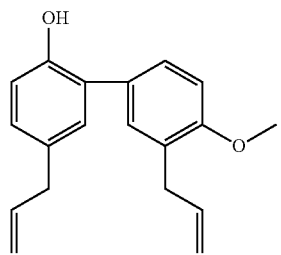 [SMILES: C=CCc1ccc(O)c(-c2ccc(OC)c(CC=C)c2)c1]

The compound represented by the above formula may have various pharmaceutically acceptable salts due to the hydroxyl group. Unless specified otherwise, the pharmaceutically acceptable salt includes all possible hydroxyl salts, including alkali metal salts such as lithium, sodium and potassium salts and alkaline earth metal salts such as magnesium and calcium salts.

Specifically, it may include physiologically acceptable salts with sodium, potassium, calcium, etc. These salts may be prepared according to the methods known in the art.

The 4-O-methylhonokiol is commercially available or may be synthesized from a commercially available compound. But, preferably, it may be isolated from plants, especially *Magnolia officinalis* Rehd. et Wils. extract. The method for isolating the 4-O-methylhonokiol from the *Magnolia officinalis* Rehd. et Wils. extract may be found in Korean Patent Application No. 10-2008-0019904 ("Composition for preventing baldness and promoting hair growth comprising extract of *Magnolia officinalis* Rehd. et Wils. or 4-O-methylhonokiol isolated therefrom") filed by the inventors of the present disclosure.

Specifically, a crude extract of *Magnolia officinalis* Rehd. et Wils. may be obtained by as follows. The leaves or barks of *Magnolia officinalis* Rehd. et Wils. are dried and extracted with about 1-20 times, specifically about 2-5 times, the weight of water, $C_1$-$C_4$ low alcohol or a mixture thereof, specifically with a mixture of water and ethanol, more specifically with 75-100% ethanol, at 0-100° C., specifically at 10-30° C., for about 1 hour to 15 days, specifically about 2-7 days, by hot water extraction, reflux cooling extraction, ultrasonic extraction, etc, specifically by reflux cooling extraction. The resultant extract may be concentrated under reduced pressure at 20-100° C., specifically at 50-70° C. to obtain the crude extract of *Magnolia officinalis* Rehd. et Wils.

A *Magnolia officinalis* Rehd. et Wils. extract soluble in a nonpolar solvent may be prepared from the *Magnolia officinalis* Rehd. et Wils. crude extract as follows. The *Magnolia officinalis* Rehd. et Wils. crude extract is dispersed in about 1-15 times, specifically about 1-10 times, the weight of water, and hexane, chloroform, methylene chloride, ethyl acetate, glycerin or propylene glycol, specifically hexane, chloroform or ethyl acetate, more specifically hexane, about 0.1-0.5 time the volume of the water is added. Then, through fractionation for 1-5 times, specifically 2-4 times, the *Magnolia officinalis* Rehd. et Wils. extract soluble in a nonpolar solvent may be obtained.

The 4-O-methylhonokiol may be isolated as follows.

A hexane solvent extract of *Magnolia officinalis* Rehd. et Wils. prepared by the afore-described method is dissolved in $C_1$-$C_4$ low alcohol, specifically in methanol, adsorbed onto a C18 column, and then adsorbed onto silica gel using a 10:1 to 4:1 mixture of $C_1$-$C_4$ low alcohol, specifically methanol, and water. Then, after isolating active fractions through silica gel column chromatography for 2-5 times, the 4-O-methylhonokiol of the present disclosure may be obtained by high-performance liquid chromatography.

Further, the 4-O-methylhonokiol effective for treating or preventing amyloid-related diseases may be synthesized by introducing substituents and performing fractionation. Also, it may be synthesized from methylation of honokiol, which is commercially available (Chengdu Biopurify Phytochemicals Ltd., CN) [Yoshiyasu F. et al., *Tetrahedron*, 48(3), p. 277-392, 1992; James K. N. et al., *Phytochemistry*, 30(7), p. 2193-2195, 1991; Shoji Y. et al., *Chem. Pharm. Bull.*, 39(8), p. 2024-2036, 1991; Herbert O. House, Modern Synthetic Reactions, 2nd ed., The Benjamin/Cummings Publishing Co., 1972].

Also, the 4-O-methylhonokiol of the present disclosure may be prepared into a pharmaceutically acceptable nontoxic salt or solvate according to a method well known in the art.

Of the pharmaceutically acceptable salts, an acid addition salt prepared from a free acid is useful. The acid addition salt may be prepared by the common method. For example, the compound is dissolved in excess aqueous acid solution, and the salt is obtained by precipitating with a water-miscible organic solvent such as methanol, ethanol, acetone or acetonitrile. After heating with equimolar acid in water or alcohol (e.g., glycol monomethyl ether), the mixture is dried by evaporation, or the precipitated salt is filtered by suction.

Unless specified otherwise, the pharmaceutically acceptable salt of the compound of the present disclosure includes a plausible acidic or basic salt of the compound. For example, the pharmaceutically acceptable salt includes sodium, calcium and potassium salts having a hydroxyl group. Further, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) having an amino group may be included. However, the pharmaceutically acceptable salt is not limited thereto, and may be prepared by the methods well known in the art.

Specifically, the composition of the present disclosure may comprise the 4-O-methylhonokiol in an amount of 0.0001-90 wt % based on the total weight.

The composition may be a pharmaceutical or functional food composition.

Specifically, the composition of the present disclosure may be in the form of powder, granule, tablet, capsule, injection, cream, gel, patch, spray or ointment.

In another aspect, the present disclosure provides a method for treating or preventing amyloid-related diseases comprising administering a pharmaceutically effective dosage of 4-O-methylhonokiol or pharmaceutically acceptable salt thereof to a subject in need thereof.

[Pharmaceutical Composition]

The pharmaceutical composition comprising 4-O-methylhonokiol as an active ingredient may further comprise a suitable carrier, excipient or diluent commonly used in the preparation of a pharmaceutical composition.

The pharmaceutical composition comprising 4-O-methylhonokiol as an active ingredient may be formulated into powder, granule, tablet, capsule, suspension, emulsion, syrup, aerosol or sterilized injection solution according to common methods.

The carrier, excipient or diluent that may be included in the composition comprising 4-O-methylhonokiol as an active ingredient may be lactose, dextrose, sucrose, oligosaccharide, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate or mineral oil. In case of formulating, diluents or excipients such as fillers, extenders, binders, wetting agents, disintegrants, surfactants, etc. may be used. Solid preparations for oral administration include tablet, pill, powder, granule, capsule, etc. and are prepared by mixing with one or more excipients, for example, starch, calcium carbonate, sucrose or lactose, gelatin, etc. Also, in addition to simple excipients, lubricants such as magnesium stearate or talc may be used. Liquid formulations for oral administration include suspension, internal solution, emulsion, syrup, etc. In addition to simple diluents such as water and liquid paraffin, various excipients, e.g. wetting agent, sweetener, aromatic, preservative, etc., may be included. Formulations for parenteral administration include sterilized water aqueous, non-aqueous solution, suspension, emulsion, lyophilization preparation, or suppository. Propylene glycol, polyethylene glycol, vegetable oil such as olive oil, injectable ester such as ethyl oleate, etc. may be used as the non-aqueous solution or suspension. Witepsol, macrogol, Tween 61, cocoa butter, laurin butter, glycerogelatin, etc. may be used as a base of the suppository.

The pharmaceutically effective dosage of the compound of the present disclosure is different depending on condition and body weight of a patient, severity of disease, formulation type, route and period of administration, and the like. The dosage may be selected appropriately by those skilled in the art. To achieve a desirable effect, the compound of the present disclosure may be administered with a dosage of 0.0001-100 mg/kg, specifically 0.001-10 mg/kg a day. The administration may be made once or several times a day. However, the aforesaid dosage does not limit the scope of the present disclosure by any means.

The compound of the present disclosure may be administered via various routes. All possible routes of administration may be expected, including, for example, oral, rectal, intravenous, intramuscular, subcutaneous, intrauterine or intracerebroventricular routes.

[Functional Food Composition]

The functional food composition of the present disclosure for treating or preventing amyloid-related diseases may further comprise a sitologically acceptable food additive, and may be prepared into pill, powder, granule, infusion, tablet, capsule or drink.

The 4-O-methylhonokiol of the present disclosure may also be used as a food additive of a health supplement food for preventing Alzheimer's disease and other amyloid-related diseases. The food comprising the 4-O-methylhonokiol of the present disclosure may be in various food forms, e.g., drink, gum, tea, vitamin complex, health supplement food, etc., and may be prepared into pill, powder, granule, infusion, tablet, capsule or drink.

In the food or drink, the 4-O-methylhonokiol may be generally included in an amount from 0.0001-90 wt %, based on the total weight of the health food composition, or in an amount from 00.0001-20 wt %, based on 100 mL of the health drink composition.

As used herein, the food additive includes those commonly used in the related art, for example, flavor, sweetener, colorant, filler, stabilizer, and the like.

The health drink composition of the present disclosure may include various ingredients, as long as it includes the 4-O-methylhonokiol with the above-described amount. For example, various flavors or natural carbohydrates may be added. Examples of the natural carbohydrate include commonly used sugars such as monosaccharides like glucose, fructose, etc., disaccharides like maltose, sucrose, etc. and polysaccharides like dextrin, cyclodextrin, etc., and sugar alcohols such as xylitol, sorbitol, erythritol, etc. In addition, natural flavors [thaumatin, stevia extract (e.g., rebaudioside A, glycyrrhizin, etc.)] and synthetic flavors (saccharin, aspartame, etc.) may be advantageously used. In general, the natural carbohydrate is included in an amount from 1 to 20 g, specifically about from 5 to 12 g, based on 100 mL of the composition of the present disclosure.

In addition, the composition of the present disclosure may further comprise various nutrients, vitamins, minerals (electrolytes), synthetic or natural sweeteners, colorants and extenders (cheese, chocolate, etc.), pectic acid and salts thereof, alginic acid and salts thereof, organic acids, protective colloid thickeners, pH control agents, stabilizers, antiseptics, glycerin, alcohol, carbonated agents used in carbonated drinks, etc. Further, the composition of the present disclosure may comprise natural fruit juice and pulp for preparing fruit juice beverage and vegetable beverage. Such ingredients can be used alone or in combination. The ratio of the additive is not important, but is generally selected from the range of 0-20 parts by weight, based on 100 parts by weight of the composition of the present disclosure.

MODE FOR INVENTION

The following examples illustrate the present disclosure and are not intended to limit the same.

Example 1

Preparation of *Magnolia Officinalis* Rehd. et Wils. Crude Extract Soluble in Polar Solvent The bark of *Magnolia officinalis* Rehd. et Wils. purchased at Gyeongdong Market was dried and finely chopped. The resulting bark (3 kg) was extracted 3 times at room temperature by adding 95% ethanol (9 L). After filtration, the filtrate was concentrated under reduced pressure using a concentrator (Eyela, N-1000, Japan). 470 g of a dried crude extract, which was used in the following example.

Example 2

Preparation of *Magnolia Officinalis* Rehd. et Wils. Extract Soluble in Nonpolar Solvent The *Magnolia officinalis* Rehd. et Wils. crude extract (200 g) obtained in Example 1 was suspended in distilled water (2 L), dissolved by adding hexane (500 mL), and then subjected to fractional extraction. This procedure was repeated twice. The hexane layer was concentrated under reduced pressure to obtain the *Magnolia officinalis* Rehd. et Wils. extract soluble in hexane (70 g), which was used in the following example.

Example 3

Isolation of 4-O-methylhonokiol from *Magnolia officinalis* Rehd. et Wils. Extract The *Magnolia officinalis* Rehd. et Wils. extract soluble in hexane (70 g) obtained in Example 2 was dissolved in methanol (300 mL) and adsorbed to a C18 column (300 g). A fraction was obtained using a mixture solution of methanol and water (4:1). The eluate was concentrated under reduced pressure. Thus obtained yellowish brown concentrate (40 g) was dissolved in methylene chloride. After packing silica gel (1 kg, Merck, product name: 9385) in a column (4.5×40 cm) using a mixture solution of hexane and ethyl acetate (9:1), the fraction was adsorbed to the silica gel, and silica gel column chromatography was performed twice, while varying the proportion of hexane to ethyl acetate from 9:1 to 6:4. Finally, 4-O-methylhonokiol (2 g) was purified by high-performance liquid chromatography under the condition described in Table 1, which was used in the following examples.

The 4-O-methylhonokiol was analyzed by $^1$H-NMR (Varian, Gemini, 400 MHz) and $^{13}$C-NMR (Varian, Gemini, 100 MHz). $CDCl_3$ (chloroform-d, Aldrich) was used as solvent, and trimethylsilane was used as internal standard. The NMR data coincided with the previously published ones [Shoji Y. et al., *Chem. Pharm. Bull.* 39, p. 2024, 1991].

$^1$H-NMR (400 MHz, $CDCl_3$): δ ppm 3.45 (2H, d, J=6.0 Hz, H-7'), 3.45 (2H, d, J=6.0 Hz, H-7), 3.90 (3H, s, OMe), 5.10 (4H, m, H-9 and H-9'), 6.01 (2H, m, H-8 and H-8'), 6.95 (1H, dd, J=8, 1.5 Hz, H-3'), 6.97 (1H, dd, J=8.0, 1.5 Hz, H-3), 7.05 (2H, m, H-2 and H-6'), 7.23 (1H, dd, J=8.5, 1.6 Hz, H-6), 7.30 (1H, dd, J=8.5, 1.6 Hz, H-4');

$^{13}$C-NMR (100 MHz, $CDCl_3$): δ ppm 34.22 (C-7), 39.36 (C-7'), 55.47 (OMe), 110.88 (C-3'), 115.47 (C-9), 115.53 (C-9'), 115.77 (C-5), 127.83 (C-1'), 127.86 (C-6), 128.67 (C-3), 129.09 (C-1), 129.64 (C-4'), 130.46 (C-61), 130.67 (C-2), 132.09 (C-5'), 136.48 (C-8), 137.77 (C-8'), 150.79 (C-2'), 156.94 (C-4).

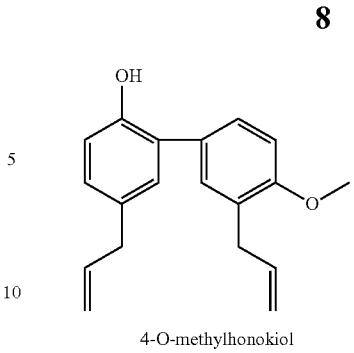

4-O-methylhonokiol

TABLE 1

| Column | Shim-Pak prep-ODS column (Shimadzu) |
|---|---|
| Column temperature | 30° C. |
| Flow rate | 18 mL/min |
| Detector | UV detector, 254 nm |
| Injection volume | 400 μL |
| Mobile phase | 80% methanol |

Test Example 1

Water Maze Test for Evaluating Spatial Learning Ability

In order to test the effect of 4-O-methylhonokiol on the scopolamine-induced impairment of learning ability of mice, experiment was performed as follows based on the water maze test animal model described in the literature [Korea Health Research Association, Guidelines for the Testing of Functional Health Foods, 663-701, 2004; Widy-Tyszkiewicz et al., *Biol. Pharm. Bull.*, 2002]. 5-6 weeks old male ICR mice (20-28 g; Dae Han Biolink, Korea) were raised under controlled lighting (12-hour light-dark cycle) and temperature (22±2° C.) conditions. They were grouped (n=10) and given free access to food and water, in a cage. The mice were accustomed for a week before performing the test.

A round pool 180 cm in diameter and 50 cm in height was filled with water (22±3° C.) to 30 cm in depth. A transparent acryl resin platform (diameter 12 cm) was placed 1.5 cm below the surface of the water. The mice were trained for 6 days, 180 seconds a day (acquisition test). On day 7, retention test was carried out. The mice were forced to swim for 60 seconds by removing the platform. All the behaviors of the mice were recorded using a video camera. Time and distance were measured until the mice climbed onto the platform.

Scopolamine (0.1 mg, Wako, Japan) dissolved in ethanol (0.1 mL) was diluted with 0.1% Tween-80, in order to abdominally administer 0.1 mL per 10 g of body weight (1 mg/kg). 4-O-methylhonokiol (0.5, 1 and 1.5 mg/kg) was dissolved in drinking water and orally administered to the mice, for a week. The comparison group was treated with scopolamine only, and the control group was not treated with any substance. Test result is given in Table 2.

TABLE 2

| Test groups | Escape distance (cm) | Improvement (%) |
|---|---|---|
| Control group | 232 | — |
| Comparison group (scopolamine 1 mg/kg) | 884 | 0 |
| Scopolamine 1 mg/kg + | 566 | 48.8 |

TABLE 2-continued

| Test groups | Escape distance (cm) | Improvement (%) |
| --- | --- | --- |
| 4-O-methylhonokiol 0.5 mg/kg | | |
| Scopolamine 1 mg/kg + 4-O-methylhonokiol 1 mg/kg | 305 | 88.6 |
| Scopolamine 1 mg/kg + 4-O-methylhonokiol 1.5 mg/kg | 284 | 91.8 |

As seen in Table 2, the mice treated with scopolamine only exhibited increased escape distance, whereas those treated with scopolamine together with 4-O-methylhonokiol exhibited significant, concentration-dependent decrease of escape distance, to a level similar to the control group.

Test Example 2

Passive Avoidance Test for Evaluating Explicit Memory

In order to test the effect of 4-O-methylhonokiol on the scopolamine-induced impairment of memory of mice, experiment was performed as follows based on the passive avoidance test animal model described in the literature [Korea Health Research Association, Guidelines for the Testing of Functional Health Foods, 663-701, 2004; Rho et al., *Biol. Pharm. Bull.*, 2005].

A passive avoidance instrument consisting of two chambers separated by a guillotine door was used as the experimental apparatus. One chamber was an illuminated chamber made of transparent acryl boards (30×30×30 cm) and the other was a dark chamber made of black acryl boards (same dimensions). The floor of the dark chamber was equipped with a grid made of aluminum pieces separated by a regular spacing. The grid was connected to an apparatus for delivering electric shocks to the feet of the test animal. A mouse was put into the illuminated chamber and the guillotine door was opened so that the mouse could enter the dark chamber. The acquisition trials were repeated 3 times. On the third run, immediately after the mouse entered the dark chamber, an electric shock was delivered through the aluminum grid (0.1 mA, 5 seconds). Memory test was performed 24 hours after the acquisition trials. The mouse was put into the illuminated chamber, the guillotine door was opened, and the time taken for the mouse to enter the dark chamber was measured (step-through latency). A longer time means better learning ability and memory. 10 mice were tested for each group. The result is given in Table 3.

TABLE 3

| Test groups | Step-through latency (sec) | Improvement (%) |
| --- | --- | --- |
| Control group | 34.3 | — |
| Comparison group (scopolamine 1 mg/kg) | 14.6 | 0 |
| Scopolamine 1 mg/kg + 4-O-methylhonokiol 0.5 mg/kg | 21.9 | 37.1 |
| Scopolamine 1 mg/kg + 4-O-methylhonokiol 1 mg/kg | 28.3 | 70 |
| Scopolamine 1 mg/kg + 4-O-methylhonokiol 1.5 mg/kg | 33.5 | 95 |

As seen in Table 3, the mice treated with scopolamine only exhibited decreased step-through latency, whereas those treated with scopolamine together with 4-O-methylhonokiol exhibited significant, concentration-dependent increase of step-through latency, to a level similar to the control group.

Test Example 3

Inhibition of Acetylcholinesterase Activity

After the behavioral pharmacological experiments, the brain cortex and hippocampus were separated from the brain of the mouse, homogenized with RO-PREP protein extraction solution (iNtRON Biotechnology), and centrifuged at 4° C., at 15,000 rpm, for 2 hours. The protein quantity of the supernatant was analyzed with a Bio-Rad protein analysis kit (Bio-Rad). Acetylcholinesterase activity was analyzed by the modified Ellman's method.

Cell lysate was put in a 96-well plate, 10 μL per well. After adding reaction buffer [190 μL, 0.01% DTNB, 0.02% acetylthiocholine and 0.1 mM isoOMPA in 50 mM Tris-HCl (pH 8.0, 0.1 M NaCl, 20 mM $MgCl_2$)], measurement was made at 37° C., at 405 nm, for 5 minutes. After 10 minutes of reaction, measurement was made again at the same wavelength. After adding different concentrations of acetylcholinesterase and treating with standard buffer [0.01% DTNB and 0.02% 0.1 mM isoOMPA in 50 mM Tris-HCl (pH 8.0, 0.1 M NaCl, 20 mM $MgCl_2$)], measurement was made at 37° C., at 405 nm, for 5 minutes. Activity was calculated from the difference of absorbance at the first and second measurements. The result is given in Tables 4 and 5.

TABLE 4

| Test groups | Enzyme activity | Improvement (%) |
| --- | --- | --- |
| Control group | 17.5 | — |
| Comparison group (scopolamine 1 mg/kg) | 39.7 | 0 |
| Scopolamine 1 mg/kg + 4-O-methylhonokiol 0.5 mg/kg | 30.2 | 42.8 |
| Scopolamine 1 mg/kg + 4-O-methylhonokiol 1 mg/kg | 24.1 | 70.3 |
| Scopolamine 1 mg/kg + 4-O-methylhonokiol 1.5 mg/kg | 19.1 | 92.8 |

As seen in Table 4, the cortices treated with scopolamine only exhibited increased enzyme activity, whereas those treated with scopolamine together with 4-O-methylhonokiol exhibited significant, concentration-dependent decrease of enzyme activity, to a level similar to the control group.

TABLE 5

| Test groups | Enzyme activity | Improvement (%) |
| --- | --- | --- |
| Control group | 12.9 | — |
| Comparison group (scopolamine 1 mg/kg) | 17.3 | 0 |
| Scopolamine 1 mg/kg + 4-O-methylhonokiol 0.5 mg/kg | 14.1 | 72.7 |
| Scopolamine 1 mg/kg + 4-O-methylhonokiol 1 mg/kg | 13.2 | 93.2 |
| Scopolamine 1 mg/kg + 4-O-methylhonokiol 1.5 mg/kg | 13 | 97.7 |

As seen in Table 4, the hippocampi treated with scopolamine together with 4-O-methylhonokiol exhibited significant, concentration-dependent decrease of enzyme activity, to a level similar to the control group, as in the cortices.

Test Example 4

Comparison of inhibition of Acetylcholinesterase Activity by Honokiol and 4-O-Methylhonokiol Acetylcholinesterase activity was analyzed by the modified Ellman's method [Ellman G. L., et al., *Biochem. Pharmacol.* 7, 88-95, 1961]. After adding 50 mM phosphate buffer (30 μL, pH 8.0) to a 96-well plate, different concentrations of 4-O-methylhonokiol or honokiol was added, 10 μL per well, and acetylcholinesterase was added, 10 μL per well. Then, 50 mM phosphate buffer (50 μL, pH 8.0) containing 0.5 mM acetylthiocholine iodide and 1 mM 5,5'-dithiobis(2-nitrobenzoic acid) was added as a substrate for the enzyme. After 5 minutes of reaction at 25° C., absorbance was measured at 412 nm. The inhibition of acetylcholinesterase activity was calculated by the following equation. Measurement was made 3 times. The result is given in Table 6.

Inhibition of acetylcholinesterase activity (%)=[1−ODs/(ODb−ODc)]×100 wherein

ODb: absorbance of untreated reaction solution at 412 nm;

ODs: absorbance of treated reaction solution at 412 nm; and

ODc: absorbance of control at 412 nm.

TABLE 6

| | Concentration | Inhibition (%) | IC$_{50}$ |
|---|---|---|---|
| 4-O-methylhonokiol | 1 nM | 47 | 1.2 nM |
| | 10 nM | 68 | |
| | 100 nM | 78 | |
| Honokiol | 10 nM | 17 | 250 nM |
| | 100 nM | 43 | |
| | 1000 nM | 74 | |

As seen in Table 6, 4-O-methylhonokiol (IC$_{50}$=1.2 nM) showed about 200 times better inhibition ability of acetylcholinesterase activity than honokiol (IC$_{50}$=250 nM).

Test Example 5

Inhibition of amyloid-β 1-42 production

After the behavioral pharmacological experiments, the brain cortex and hippocampus were separated from the brain of the mouse, homogenized with RO-PREP protein extraction solution, and centrifuged at 4° C., at 15,000 rpm, for 2 hours. The protein quantity of the supernatant was analyzed with a Bio-Rad protein analysis kit (Bio-Rad). Amyloid-β 1-42 were quantitated using an amyloid beta 1-42 assay kit (Immuno-Biological, Japan).

The protein extract (100 μL) obtained from the brain cortex or hippocampus was put in a coated 96-well plate and incubated at 4° C. overnight. After washing with washing buffer and adding labeled antibody solution, the mixture was incubated at 4° C. for 1 hour in the dark. After washing again and adding chromogen, the mixture was incubated at room temperature for 30 minutes in the dark. Then, after adding stop solution, absorbance was measured at 450 nm. Measurement was made 3 times. The result is given in Tables 7 and 8.

TABLE 7

| Test groups | Production amount | Improvement (%) |
|---|---|---|
| Control group | 23.5 | — |
| Comparison group (β-amyloid 1 mg/kg) | 28.1 | 0 |
| β-amyloid 1 mg/kg + 4-O-methylhonokiol 0.5 mg/kg | 26.8 | 28.3 |
| β-amyloid 1 mg/kg + 4-O-methylhonokiol 1 mg/kg | 24.3 | 82.6 |
| β-amyloid 1 mg/kg + 4-O-methylhonokiol 1.5 mg/kg | 23.1 | 100 |

As seen in Table 7, the cortices treated with β-amyloid only exhibited increased β amyloid, whereas those treated with β-amyloid together with 4-O-methylhonokiol exhibited significant, concentration-dependent decrease of β-amyloid.

TABLE 8

| Test groups | Production amount | Improvement (%) |
|---|---|---|
| Control group | 16.2 | — |
| Comparison group (β-amyloid 1 mg/kg) | 25.1 | 0 |
| β-amyloid 1 mg/kg + 4-O-methylhonokiol 0.5 mg/kg | 22.7 | 33.3 |
| β-amyloid 1 mg/kg + 4-O-methylhonokiol 1 mg/kg | 18.2 | 77.8 |
| β-amyloid 1 mg/kg + 4-O-methylhonokiol 1.5 mg/kg | 16.5 | 95.6 |

As seen in Table 8, the hippocampi treated with β-amyloid only exhibited increased β amyloid as in the cortices, whereas those treated with β-amyloid together with 4-O-methylhonokiol exhibited significant, concentration-dependent decrease of β-amyloid.

Formulation Example 1

Powder

| Ingredients | Contents |
|---|---|
| 4-O-methylhonokiol | 300 mg |
| Lactose | 100 mg |
| Talc | 10 mg |

The above ingredients are mixed and filled in an airtight pouch to prepare powder.

Formulation Example 2

Tablet

| Ingredients | Contents |
|---|---|
| 4-O-methylhonokiol | 50 mg |
| Cornstarch | 100 mg |
| Lactose | 100 mg |
| Magnesium stearate | 2 mg |

The above ingredients are mixed and compounded according to a common method to prepare a tablet.

Formulation Example 3

Capsule

| Ingredients | Contents |
|---|---|
| 4-O-methylhonokiol | 50 mg |
| Cornstarch | 100 mg |
| Lactose | 100 mg |
| Magnesium stearate | 2 mg |

The above ingredients are mixed and filled in a gelatin capsule according to a common method to prepare a capsule.

Formulation Example 4

Injection

| Ingredients | Contents |
|---|---|
| 4-O-methylhonokiol | 50 mg |
| Distilled water for injection | adequate |
| pH control agent | adequate |

The above ingredients are mixed and prepared into injection, with the above contents per 2-mL ampule.

Formulation Example 5

Liquid

| Ingredients | Contents |
|---|---|
| 4-O-methylhonokiol | 100 mg |
| Isomerized sugar | 10 g |
| Mannitol | 5 g |
| Purified water | adequate |

The above ingredients are dissolved in purified water. After adding an adequate amount of lemon flavor, the ingredients are mixed and purified water is added to make 100 mL. The resulting liquid is put in a brown bottle and sterilized.

Formulation Example 6

Health Food

| No. | Ingredients | Contents |
|---|---|---|
| 1 | 4-O-methylhonokiol | 1000 mg |
| 2 | Vitamin complex | adequate |
| 3 | Vitamin A acetate | 70 μg |
| 4 | Vitamin E | 1.0 mg |
| 5 | Vitamin $B_1$ | 0.13 mg |
| 6 | Vitamin $B_2$ | 0.15 mg |
| 7 | Vitamin $B_6$ | 0.5 mg |
| 8 | Vitamin $B_{12}$ | 0.2 μg |
| 9 | Vitamin C | 10 mg |
| 10 | Biotin | 10 μg |
| 11 | Nicotinamide | 1.7 mg |
| 12 | Folic acid | 50 μg |
| 13 | Calcium pantothenate | 0.5 mg |
| 14 | Mineral complex | adequate |
| 15 | Iron(I) sulfate | 1.75 mg |
| 16 | Zinc oxide | 0.82 mg |
| 17 | Magnesium carbonate | 25.3 mg |
| 18 | Potassium phosphate monobasic | 15.0 mg |
| 19 | Calcium phosphate dibasic | 55.0 mg |
| 20 | Potassium citrate | 90.0 mg |
| 21 | Calcium carbonate | 100.0 mg |
| 22 | Magnesium chloride | 24.8 mg |

The contents described above are given as a specific example, but may be changed as required. The above ingredients may be mixed by the method commonly used in the art to prepare granule, and then prepared into a health food composition according to the method commonly used in the art.

Formulation Example 7

Health Drink

| No. | Ingredients | Contents |
|---|---|---|
| 1 | 4-O-methylhonokiol | 1000 mg |
| 2 | Citric acid | 1000 mg |
| 3 | Oligosaccharide | 100 g |
| 4 | Plum concentrate | 2 g |
| 5 | Taurine | 1 g |
| 6 | Purified water | to make 900 ml |

The above ingredients are mixed and heated at 85° C. for about 1 hour while stirring. Thus obtained solution is put in a sterilized 2-L container and kept at low temperature after sealing and sterilization.

The contents described above are given as a specific examples but may be varied depending on the customers, region, purpose of use, and the like.

INDUSTRIAL APPLICABILITY

As described, the pharmaceutical composition comprising 4-O-methylhonokiol as an active ingredient inhibits β-amyloid production, and thus can be effectively used as a functional food or pharmaceutical composition for treating or preventing amyloid-related diseases such as Alzheimer's disease, defective memory, cognitive disorder, amyloidosis, etc.

The present disclosure has been described in detail with reference to preferred embodiments thereof. However, it will be appreciated by those skilled in the art that changes may be made in these embodiments without departing from the principles and spirit of the disclosure, the scope of which is defined in the appended claims and their equivalents.

The invention claimed is:
1. A method for reducing beta-amyloid comprising administering a pharmaceutically effective dosage of 4-O-methylhonokiol or a pharmaceutically acceptable salt thereof to a subject in need thereof.

2. The method according to claim 1, wherein the pharmaceutically acceptable salt is a metal salt with lithium, sodium, potassium, calcium or magnesium bound to the hydroxyl group of the 4-O-methylhonokiol.

3. The method according to claim 1, wherein the 4-O-methylhonokiol is isolated from *Magnolia officinalis* Rehd. et Wils. extract.

4. The method according to claim 1, wherein the 4-O-methylhonokiol is chemically synthesized from methylation of honokiol.

5. The method according to claim 1, wherein the subject has a beta-amyloid-related disease selected from a group consisting of Alzheimer's disease, cognitive disorder, defective memory and amyloidosis.

6. The method according to claim 1, wherein the 4-O-methylhonokiol or a pharmaceutically acceptable salt thereof is administered as a composition comprising the 4-O-methylhonokiol or the pharmaceutically acceptable salt thereof in an amount of 0.0001-90 wt % based on the total weight.

7. The method according to claim 6, wherein the composition is a pharmaceutical or functional food composition.

8. The method according to claim 6, wherein the composition is in the form of powder, granule, tablet, capsule, injection, cream, gel, patch, spray or ointment.

* * * * *